United States Patent [19]
Binot et al.

[11] Patent Number: 5,290,700
[45] Date of Patent: Mar. 1, 1994

[54] CELL CULTURE DEVICE

[75] Inventors: Patrick Binot, Bussy St. Georges; Dominique Cognard, Guyancourt; Frédéric Dufau, La Celle-Saint-Cloud; Jean Hache, Trappes, all of France

[73] Assignee: Bertin & Cie., Plaisir, Cedex

[21] Appl. No.: 773,609

[22] PCT Filed: Mar. 28, 1991

[86] PCT No.: PCT/FR91/00246
§ 371 Date: Jan. 14, 1992
§ 102(e) Date: Jan. 14, 1992

[87] PCT Pub. No.: WO91/15570
PCT Pub. Date: Oct. 17, 1991

[30] Foreign Application Priority Data

Mar. 30, 1990 [FR] France ................. 90/94092

[51] Int. Cl.$^5$ ............. C12M 3/00; C12M 3/04; C12M 1/00; C12M 1/12
[52] U.S. Cl. .................... 435/284; 435/285; 435/287; 435/311
[58] Field of Search ............. 435/287, 284, 285, 311

[56] References Cited

U.S. PATENT DOCUMENTS

| | | | |
|---|---|---|---|
| 3,883,393 | 5/1975 | Knazek et al. | 435/284 |
| 4,087,327 | 5/1978 | Feder et al. | 435/287 |
| 4,220,725 | 9/1980 | Knazek et al. | 435/285 |
| 4,442,206 | 4/1984 | Michaels et al. | 435/284 |
| 4,610,789 | 9/1986 | Barch | 210/321.4 |

FOREIGN PATENT DOCUMENTS 0113328 7/1984 European Pat. Off.
WO8606094 10/1986 PCT Int'l Appl.
WO9013639 11/1990 PCT Int'l Appl.

OTHER PUBLICATIONS

Tharakan, J. P., et al., (1986) *Biotechnology and Bioengineering*, vol. XVIII, pp. 329-342.

Primary Examiner—Robert J. Warden
Assistant Examiner—Christopher Y. Kim
Attorney, Agent, or Firm—Walter H. Dreger; Jan P. Brunelle

[57] ABSTRACT

A cell culture device is disclosed where cells are confined in a liquid medium within a cell culture space. The cell culture space is delimited by at least three selectively permeable walls. One wall is formed by a sheet of tubes and is permeable to fresh nutrient medium, the second wall is formed of a layer of capillaries and is permeable to gaseous fluids, and the third wall acts as a micron sieve that allows the passage of spent nutrient medium, but retains the cells within the cell culture space. The cell culture device makes it possible to produce culture products, continuously and in bulk over a long period of time.

18 Claims, 3 Drawing Sheets

CELL CULTURE DEVICE

The present invention relates to a continuous bulk cell culture device, or bioreactor, which makes it possible in particular to improve the preparation of the products of said cultures.

Several cell culture methods and devices are known at the present time.

Cells can be cultured on a smooth surface such as appropriate plastic or glass (dishes or tubes). Such cultures do not permit substantial cell growth and they require large amounts of nutriments.

In particular, U.S. Pat. Nos. 3,883,393 (USA), 3,997,396 (MONSANTO Co.), 4,087,327, 4,201,845 (MONSANTO Co.), 4,220,725 (USA) and 4,391,912 describe systems in which the cells are cultivated on or near hollow fibers.

U.S. Pat. No. 4,201,845 (MONSANTO Co.) describes in particular a cell culture reactor comprising a culture chamber in which a layer of hollow fibers for supplying gas is sandwiched between a microporous membrane for distributing the culture medium and a microporous membrane acting as a barrier to diffusion of the cells out of said chamber. The flow of medium is directed upwards and transversely to the plane of the fibers.

However, this device has a number of disadvantages; in particular, there are risks that the membrane distributing culture medium will clog because of the frontal attack on said membrane, this clogging resulting in local inequalities of flow rate and non-homogeneous nutriment distribution.

In some of these devices, and especially in the MONSANTO device, the distribution of the medium towards the cells is not effected homogeneously over the whole surface of the plate; this can cause disparities, which are difficult to control, in the metabolism of the cells, according to their position in the device, and difficulties in extrapolating the size of the device, especially in the context of industrial production.

The aim of the Applicant was consequently to provide a bioreactor, or cell culture device, which meets practical needs better than the devices of the prior art, especially by making it possible to produce culture products, continuously and in bulk, from cultures kept at a high cell concentration in excess of $5.10^8/cm^3$, over a long period, without causing clogging, i.e. without reducing the flow rate of nutriments in the whole of the cell space, and to use a cell space of large dimensions which is better suited to the industrial scale.

The present invention relates to a cell culture device, or bioreactor, especially for the production of metabolites, of the type comprising a cell culture space in which the cells are confined in a liquid medium—said space being delimited by walls of which at least three are selectively permeable, the first to the fresh nutrient medium, the second to the gaseous fluids and the last to the spent nutrient medium—and means of circulating the fluids in said device, characterized in that the first wall consists of a sheet of tubes whose wall is permeable to the fresh nutrient medium, said tubes being assembled in parallel between an inlet manifold and an outlet manifold in a closed-loop circuit including means of supplying said fresh nutrient medium, and fresh medium passing through each of said tubes, from end to end, at a flow rate which is several times greater than that passing through its wall.

In terms of the present invention, fresh medium is understood as meaning a nutriment-rich medium supplied to the cells for their needs and their growth.

Spent medium is understood as meaning a nutriment-impoverished medium containing the metabolites excreted by said cells.

According to one advantageous characteristic of this device, the flow rate of the medium passing through each tube corresponds to a flow velocity of the order of 1 dm/s, which guarantees the tangential filtration of the fresh medium through the wall of said tubes.

According to another characteristic of said device, said tubes are rigid and have a diameter of the order of a centimeter, their wall having pores whose diameter allows the nutriment molecules, and especially the molecules with a molecular weight of more than 150 kDa, to pass through, and the pressure drop across their wall is about 200 mbar.

Such tubes have the advantage of being sterilizable and they make it possible to obtain a homogeneous nutriment distribution with a maximum scatter of the order of 10%.

According to yet another advantageous characteristic of this device, the loop circuit is kept under an appropriate pressure which is calculated so as to give the desired ratio of the circulating flow rate to the traversing flow rate and overcome the capillary pressure.

According to another advantageous characteristic of this device, the second wall consists of a set of capillaries whose wall is permeable to gases, said capillaries being arranged at approximately equal intervals so as to form, on one and/or the other side of the sheet of tubes, one/several subsets with homogeneous distributione for the gas exchanges with the cells.

Said subsets of capillaries can be simple, i.e. in the form of a single layer, or they can themselves be formed of several superimposed layers of mutually parallel capillaries, the capillaries of one layer extending at right-angles with the intervals between capillaries of the two adjacent layers.

The cells which can be cultured in the device of the present invention are especially microorganisms and procaryotic and eucaryotic animal or plant cells. They may have been modified and they may be bound to a support.

Said capillaries diffuse the gas which passes through them (air, $O_2$, $N_2$, CO, $CO_2$ etc.), homogeneously inside the cell culture space.

According to a preferred arrangement of this characteristic, said capillaries are hollow fibers whose diameter is of the order of a millimeter and which have a hydrophobic wall.

The increase in the distribution area for the gases, and especially for oxygen, results in a decrease in the diffusion distances and thereby permits, by virtue of more intense and more homogeneous oxygenation without mechanical stress, an appreciably improved viability of the cells as well as the discharge of the $CO_2$ produced by the cells.

Unexpectedly, the mode of supply by tangential filtration through porous tubes avoids the problems of clogging and ensures a homogeneous distribution of the medium in the culture space, thus resulting in a better productivity and homogeneity of all the cells.

Furthermore, supplying nutriments with the aid of tubes makes it possible to simplify and control the overall hydrodynamics of the bioreactor, and using a network of aeration fibers makes it possible to bring the oxygen directly to the cell medium in a large cell space and thereby independently to control the nutriment supply, the oxygenation and the extraction of the cell culture products.

According to another advantageous characteristic of this device,, the third wall comprises at least one micron sieve forming each downstream wall of the cell culture space, in order to ensure that the cells are confined while allowing the spent medium to leave.

According to one preferred arrangement of this characteristic, said micron sieve covers at least each downstream free face of the set of capillaries.

According to another preferred arrangement of this characteristic, said third wall is a porous membrane whose pores have a diameter of between 1 and 10 μm and which is advantageously selected from organic membranes and metal membranes.

According to another advantageous characteristic of a device of the invention, the capillaries are orientated parallel to the plane of the sheet of tubes.

According to a preferred arrangement of this characteristic,, the capillaries are parallel to the tubes.

According to a preferred modality of this arrangement, said capillaries are also distributed in the free cell space between the tubes.

According to another advantageous characteristic of a device of the invention, the sheet of tubes and each set or subset of capillaries are separated by a micron sieve similar to the micron sieve forming the third wall of said device.

According to another advantageous characteristic of a device of the invention, it forms a one-sided module comprising a single set of capillaries located on one side of the sheet of tubes, and at least one downstream or outlet micron sieve.

According to yet another advantageous characteristic of a device of the invention, it forms a two-sided or symmetrical module comprising at least two subsets of capillaries running respectively along each side of the sheet of tubes, and at least one downstream or outlet micron sieve covering each subset of capillaries.

According to yet another advantageous characteristic of a device of the invention, it comprises at least two superimposed symmetrical modules, the outlet spaces and intermediate micron sieves being omitted if appropriate.

Said device can also comprise an enclosure through which at least two sets of sheets of tubes pass, the space between the tubes and the end micron sieves being filled with capillaries parallel to said tubes.

As a variant, the device according to the invention comprises an enclosure through which at least two sheets of tubes pass which form alternately inlet and outlet walls for the medium and in which the space between the tubes is filled with capillaries parallel to said tubes, the outlet tubes for the medium having the properties of a micron sieve.

The bioreactor according to the invention enables a number of problems to be solved:

cells:
   increased productivity and good utilization of the volume of the cell space;
   decreased risks of damage;
   increased viability and increased and more homogeneous cell concentration through a reduction in the oxygen diffusion distance and through a homogeneous nutriment supply;
   possibility of cultivating bound cells or free cells.

nutriments:
   decreased serum requirements because of the high cell concentration, resulting in a reduced cost;
   nutriment recirculation loop;
   limitation of the risks of clogging on the feed side through the application of tangential filtration.

production:
   the device according to the invention has the advantage of being particularly well suited to industrial applications which need size extrapolation facilities.

BRIEF DESCRIPTION OF THE DRAWINGS

In addition to the foregoing arrangements, the invention also includes other arrangements which will become apparent from the following description referring to the attached drawings, in which.

It must be clearly understood, however, that these drawings and the corresponding descriptive parts are given solely in order to illustrate the subject of the invention, without in any way implying a limitation.

Figure 1:
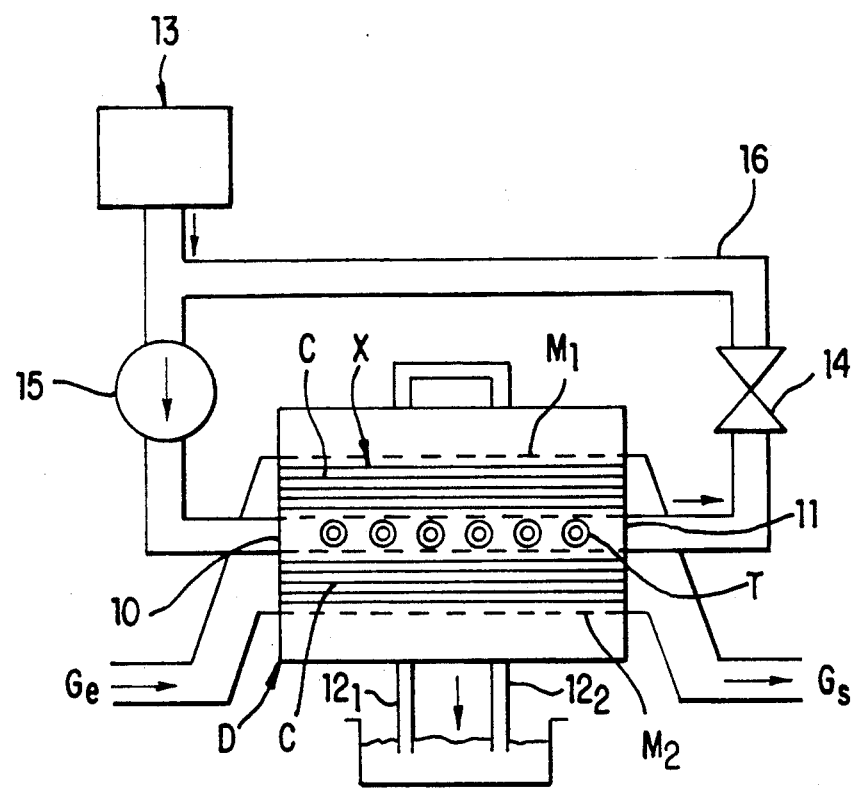
FIG. 1 is a schematic general view of a bioreactor according to the invention.

Reference is made first of all to FIGS. 1 to 4, which illustrate embodiments of the bioreactor according to the invention. FIG. 1 is a schematic view of a bioreactor according to the invention, comprising the following in a housing D delimited by a cell culture space X:

a first micron sieve $M_1$, which ensures that the cells are confined in the space X but allows the recoverable spent medium to pass through, a first subset of capillaries C, which ensure that the gaseous fluids pass through and which are arranged between the sieve $M_1$ and a sheet of tubes T, which are mutually parallel and ensure that the fresh nutrient medium passes to the cells, and a second micron sieve $M_2$, which ensures that the cells are confined in the space X, at the other end of said space, and a second subset of capillaries C arranged between the sieve $M_2$ and the sheet of tubes T.

The tubes T are assembled in parallel between two manifolds 42 and 43 (FIG. 4), which are fed in a closed-loop circuit including an inlet nozzle 10 (FIG. 1), 40 (FIG. 4) for supplying the fresh nutrient medium, and an outlet nozzle 11 (FIG. 1), 41 (FIG. 4) for said fresh medium to be recycled, these nozzles being joined together by a line 16 (FIG. 1).

Outlet pipes $12_1$ and $12_2$ for the spent medium (FIGS. 1 and 3), emerging downstream of the sieves $M_1$ and $M_2$ make it possible to extract said spent medium collected between the sieves and the housing D.

Inlet means Ge and outlet means Gs for the gaseous fluids (FIG. 2) are joined respectively to a feed volume 45 for the capillaries C and an escape volume 46 for the capillaries.

In the embodiment illustrated in FIG. 1:
the capillaries C, in the same plane, are perpendicular to the tubes T and arranged in two subsets on either side of the sheet of tubes T; and the device also comprises, associated with the line 16 for the circulation of fresh medium, means 14, 15 of placing said fresh medium under pressure. The fresh medium under pressure circulating in the tubes T, between the inlet 10 and the outlet 11, is recycled continuously in a loop fed from a reservoir 13 connected to the line 16; this makes it possible to ensure tangential filtration of said fresh medium through said tubes T in the cell culture space X.

In an advantageous embodiment of the device of the invention, the means 14 is created by a throttle valve introducing a pressure drop, and the means 15 is created by a pump.

In a variant, the bioreactor according to the invention can also comprise the following means, which are not shown in FIG. 1:

a sterile filter can be situated upstream of the gas inlet Ge;

the cell culture space X can be associated with a temperature regulating device; and the recirculation loop for fresh medium (nozzles 10 and 11) and the discharge pipes for spent medium (means $12_1$ and $12_2$) can be associated with appropriate reservoirs.

Figure 4:
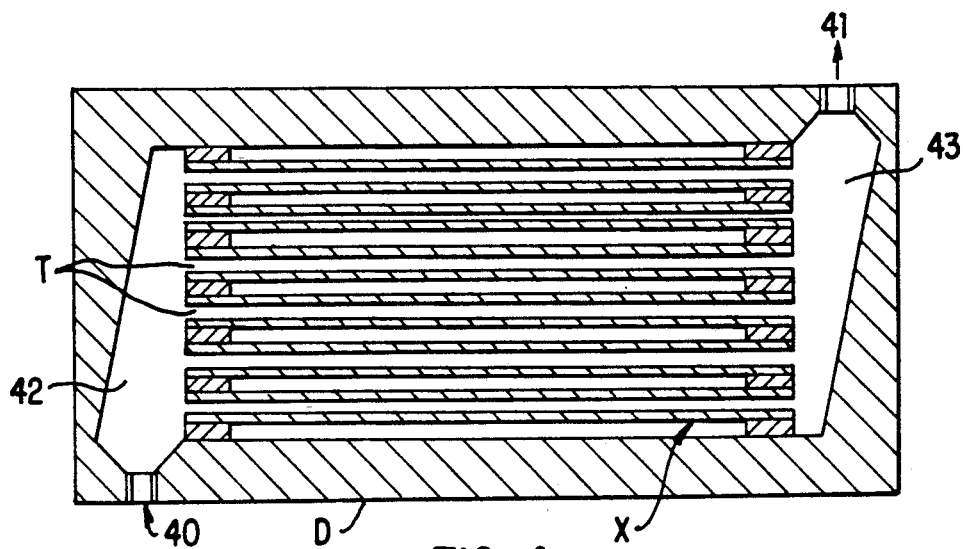
FIG. 4 is a cutaway view of the feed zone along the line 4—4 of FIG. 2.

Such bioreactors operate as follows:

After sterilization of the housing D and adjustment of the temperature, the pH, the oxygen concentration and the flow rate of appropriate medium to which serum has been added, an appropriate amount of cells is inoculated into the cell culture space X and the fresh medium is introduced via the supply means 40 into the manifold 42 (FIG. 4). The concentration of nutriments in the fresh medium, and the parameters specified above (temperature, pH, $O_2$ concentration), are monitored daily. The fresh medium flows through the tubes T at a velocity which guarantees the tangential filtration of the fresh medium through the walls of said tubes and thus ensures that the inoculated cells located in the cell culture space X are fed homogeneously. The unused fresh medium recovered at the outlet 41 via the manifold 43 is recycled continuously in a pressurized loop fed from a reservoir 13 connected to the line 16, and feeds the cells again. For its part, the spent medium is recovered, with the metabolites produced by the cells, through the outlet pipes $12_1$ and $12_2$ (FIG. 3) and subsequently treated in the appropriate manner.

Figure 2:
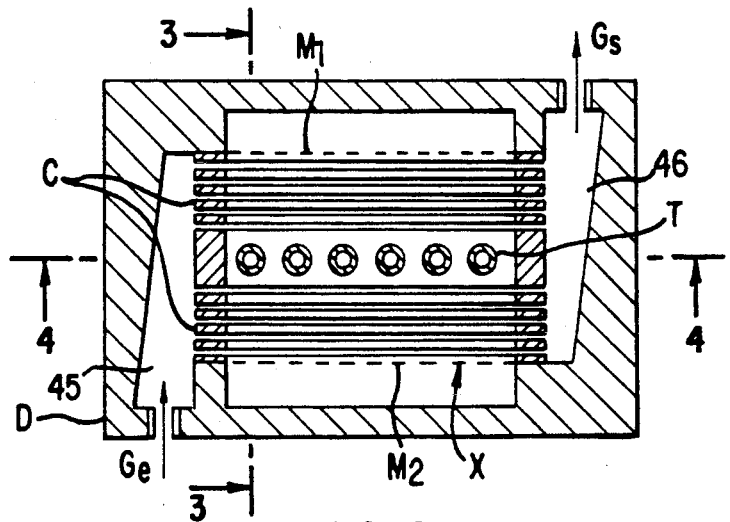
FIG. 2 is a schematic view of the bioreactor in orthogonal section relative to the tubes.
Figure 3:
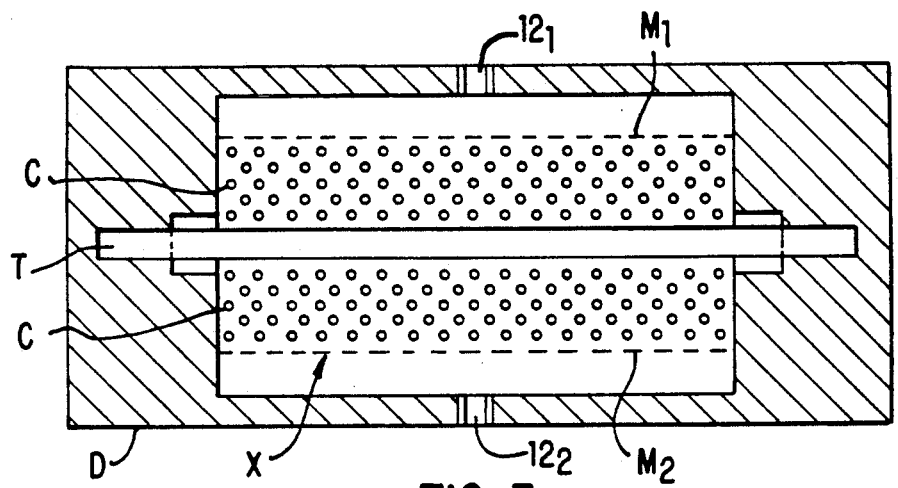
FIG. 3 is a cutaway view of the bioreactor along the line 3—3 of FIG. 2.

Simultaneously, the cells are fed with oxygen via the capillaries C, distributed uniformly in the space left free by the tubes T, in the space delimited by the end micron sieves, from a gas inlet Ge (FIG. 2). The capillaries diffuse the gas from inside each capillary towards the cells, but oppose the diffusion of liquid into said capillaries. The gas outlet Gs makes it possible to discharge the unused oxygen and also the $CO_2$ produced by the cells in culture.

Such a bioreactor, with a volume which can vary from 200 cm$^3$ to 10 l, makes it possible to carry out cultures continuously over a period of several months.

In a preferred but non-limiting embodiment of said bioreactor:

The cell culture space X is 25 mm high and is delimited by two micron sieves ($M_1$ and $M_2$, FIG. 1) of 250×400 mm.

The tubes T for supplying fresh medium have a diameter of the order of 1 cm, are rigid and have pores whose diameter allows nutriment molecules with a molecular weight of more than 150 kDa to pass through. In the embodiment shown, without implying a limitation, these tubes are made of compacted graphite covered with a sensitive layer making it possible to monitor the diameter of the pores, and have been sterilized beforehand, hand, and placing the fresh medium under pressure causes a pressure drop of more than 200 mbar when the fresh medium passes through the walls of the tubes T.

The capillaries C for supplying gaseous fluids, in the form of a plurality of porous hollow fibers regularly spaced out in the cell space X, the diameter of which is 2.6 mm in the embodiment shown, are located on either side of said tubes T, orientated parallel to the plane of the tubes T and perpendicular to the latter in said plane.

By way of example and without implying a limitation, after sterilization of the housing D, $2.10^6$ V0208 murine hybridomas, which produce a monoclonal antibody of the type IgGl, are inoculated per ml of useful volume. The experimental conditions in this case are as follows: pH for growth: 7.2; pH for antibody production: 7.05; concentration of dissolved $O_2$: about 40%; temperature: 37° C.

The fresh medium is then introduced via the inlet nozzle 40 into the manifold 42 (FIG. 4) and comprises, for example, glucose (residual concentration always greater than 0.8 g/l), glutamine (2 to 4%), amino acids (1% in the bioreactor), an RPMI 1640 medium (the recirculation rate is reduced when the lactate concentration is greater than or equal to 18 mm) and 10% foetal calf serum, the concentration of which is reduced to less than 2% from day 20 or 25. The glucose and lactate are determined daily, the glutamine and amino acids are determined regularly and the pH is measured regularly. This medium flows through the tubes T at a velocity which guarantees the tangential filtration of the above-defined fresh medium through the walls of said tubes at a velocity of the order of 10 μm/s, and ensures that the cells located in the cell culture space X are fed homogeneously.

Preferably, the flow velocity inside the tubes is of the order of 1 dm/s and the pressure is chosen so as to give the desired ratio (for example 10:1) of the circulating flow rate to the flow rate passing through the wall of the tube.

The spent medium is recovered at the outlets $12_1$ and $12_2$ and, in the embodiment shown, comprises especially the monoclonal antibodies produced by said hybridomas.

Reference is now made to the embodiments illustrated in FIGS. 5a to 5g.

Figure 5A:
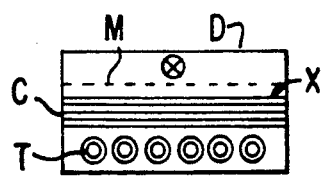
FIGS. 5a to 5g schematically show different embodiments of the bioreactor according to the invention.

FIG. 5a illustrates one embodiment of the bioreactor according to the invention, comprising a housing D which encloses a sheet of tubes T. Between the sheet of tubes T and the micron sieve M, there is a set of capillaries arranged perpendicularly to the tubes T, in the same plane, and thus forming a "one-sided module".

Figure 5B:
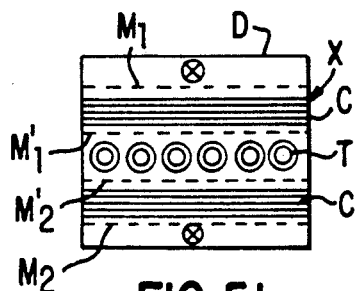

FIG. 5b illustrates another embodiment of the bioreactor according to the invention, for a "two-sided module" or symmetrical module, which comprises two subsets of capillaries C running respectively along each side of the sheet of tubes T, two end micron sieves $M_1$ and $M_2$ and two micron sieves $M'_1$ and $M'_2$ which are similar to the micron sieves $M_1$ and $M_2$ and separate each subset of capillaries C from the sheet of tubes T.

The membranes $M'_1$ and $M'_2$ make it possible to confine the cells in the space where the oxygen distribution is homogeneous (near the capillaries) and avoid clogging of the tubes.

Figure 5C:
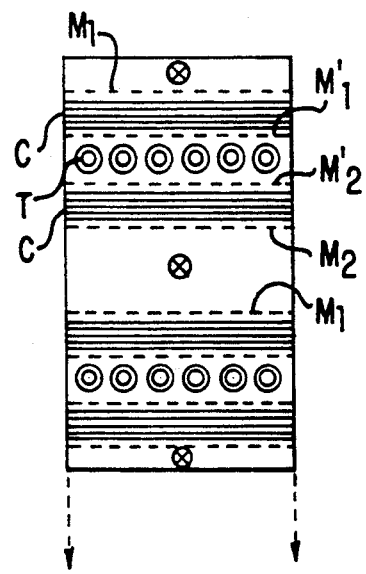

FIG. 5c illustrates an embodiment of a bioreactor according to the invention in which two symmetrical modules are superimposed between two end sieves $M_1$ and $M_2$, said bioreactor successively comprising a first subset of capillaries C, a micron sieve $M'_1$, a sheet of tubes T, a micron sieve $M'_2$, a second subset of capillaries C, a micron sieve $M_2$, an intermediate outlet space and then another symmetrical module as described above.

Figure 5D:
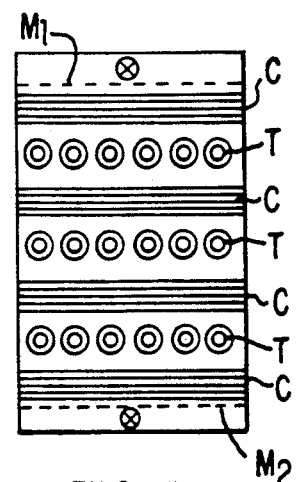

FIG. 5d illustrates an embodiment comprising a stack of several symmetrical modules as shown in FIG. 5c, the intermediate outlet space being omitted.

In FIGS. 5a to 5d above, the capillaries C are perpendicular to the tubes T in the plane of the latter, whereas in FIGS. 5e to 5g below, the tubes and the capillaries are parallel.

Figure 5E:
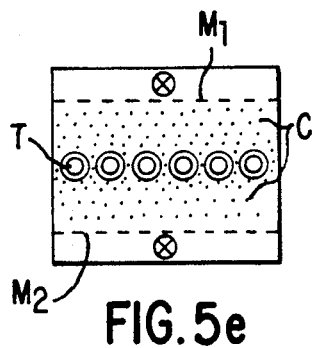

FIG. 5e schematically illustrates a two-sided or symmetrical module which comprises a set of capillaries C filling the whole of the space left free by the sheet of tubes T, between the end micron sieves $M_1$ and $M_2$.

Figure 5F:
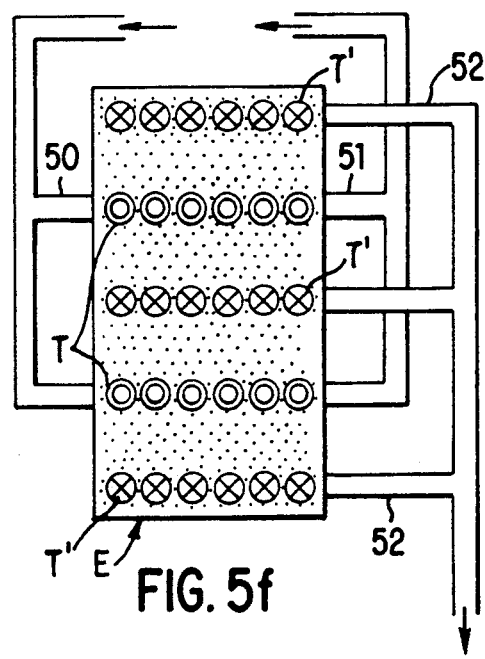

FIG. 5f schematically illustrates an embodiment in which several sheets of tubes T, T' pass through an enclosure E. The sheets of tubes T are included in the closed loops for recirculation of the fresh medium.

These sheets of tubes T' make it possible to discharge the spent medium, the tubes T' having the properties of a micron sieve M. The enclosure E also comprises a set of capillaries C parallel to the tubes T, T', which fill the whole of the cell culture space X between the tubes T and T'. The inlets 50 and outlets 51 are joined to the tubes T and the outlets 52 are joined to the tubes TI.

Figure 5G:
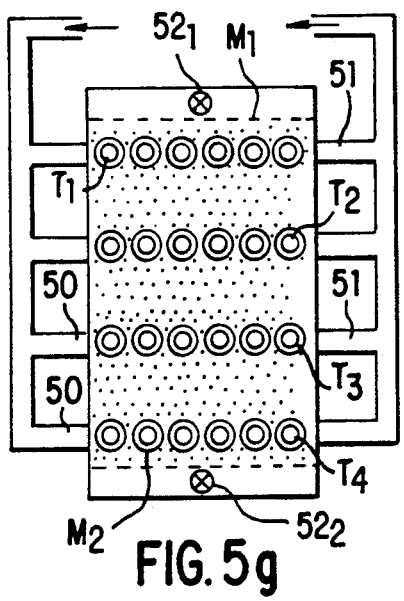

FIG. 5g illustrates an embodiment in which several sheets of tubes $T_1$, $T_2$, $T_3$, $T_4$, in which the fresh nutrient medium circulates in a closed loop, pass through an enclosure E, the latter being filled with a set of capillaries C parallel to said tubes, and also comprising two end micron sieves $M_1$ and $M_2$.

As shown in FIGS. 5f and 5g and as intended for all the variants, the sheet or sheets of tubes T are fed with fresh medium and the capillaries C are fed with appropriate gas.

As is apparent from the foregoing description, the invention is in no way limited to those embodiments and modes of application which have now been described more explicitly; on the contrary, it encompasses all the variants thereof which may occur to those skilled in the art, without deviating from the framework or the scope of the present invention.

We claim:

1. A cell culture device for the production of metabolites, comprising;
   (i) a housing (D),
   (ii) a cell culture space (X), within said housing,
   (iii) fresh nutrient medium inlet and outlet means, connected, in parallel, to a sheet of tubes (T) forming a wall of said culture space (X) and in fluid communication with said culture space,
   (iv) at least a subset of open-ended permeable capillaries (C) arranged in a layer within said culture space, whereby the open ends of said capillaries lead to external inlet and outlet gas means and in gaseous communication with the interior of said capillaries, said capillaries being arranged at approximately equal intervals so as to form, on one side of said sheet of tubes (T), one subset allowing an homogeneous distribution for the gas exchanges wit the cells,
   (v) a spent medium outlet means connected to a micron sieve (M) forming each downstream wall of the cell culture space, in order to ensure that the cells are confined while allowing the spent medium to leave,
   wherein said sheet of tubes (T), in connection with fresh nutrient medium inlet and outlet means, which are structured in a closed-loop circuit, are constructed so as to provide when fresh nutrient medium is passing through said circuit, simultaneously a first flow of fresh medium through each of said tubes, from nd to end and a second flow of fresh medium perpendicular to said first flow, from said tubes to said cell culture space (X), through their permeable walls.

2. A device according to claim 1, wherein said sheet of tubes (T) in connection with said fresh nutrient medium inlet and outlet means are constructed so as to provide said first flow velocity of 1 dm/s.

3. A device according to claim 1, wherein said tubes (T) are rigid and have a diameter of about a centimeter, their wall having pores whose diameter allows the nutriment molecules of more than 150 dKa of said nutrient medium to pass through.

4. A device according to claim 1, wherein said subset of capillaries is comprised of a single layer of capillaries.

5. A device according to claim 1, wherein said subset of capillaries is comprised of at least two superimposed layers of mutually parallel capillaries, the capillaries of one layer being parallel with the intervals between capillaries of the an adjacent layer.

6. A device according to claim 1, wherein said capillaries are hollow fibers whose diameter is about a millimeter and which have a hydrophobic wall.

7. A device according to claim 1, wherein said micron sieve (M) covers at least each downstream free face of the subset of capillaries.

8. A device according to claim 1, wherein said micron sieve forming each downstream wall of the cell culture space, is a porous membrane whose pores have a diameter of between 1 and 10 $\mu$m.

9. A device according to claim 1, wherein the capillaries (C) are oriented parallel to the plane of the sheet of tubes (T).

10. A device according to claim 9, wherein the capillaries (C) are parallel to the tubes (T).

11. A device according to claim 10, wherein said capillaries (C) are also distributed in the free cell space between the tubes (T).

12. A device according to claim 7, wherein the sheet of tubes (T) and the set or subset of capillaries (C) are separated by a micron sieve ($M'_1$, $M'_2$) having the same permeability as the micron sieve (M).

13. A device according to claim 1, wherein the set of capillaries (C) is located between the sheet of tubes (T), and at least one downstream (or outlet) micron sieve (M), so as to form a one-sided module.

14. A device according to claim 13, further comprising at least a second subset of capillaries (C) running respectively along the side of the sheet of tubes (T) opposite from that of the first subset of capillaries and a second downstream (or outlet) micron sieve ($M'_1$, $M'_2$) so as to form a two-sided or symmetrical module.

15. A device according to claim 14, further comprising at least a second symmetrical module, superimposed on the first symmetrical module, the intermediate outlet spaces and micron sieves being omitted.

16. A device according to claim 14, wherein it comprises an enclosure (E) through which at least two sets of sheets of tubes (T, T') pass which form alternately inlet and outlet walls and in which the space between the tubes is filled with capillaries (C) parallel to said tubes, the tubes (T') being permeable to spent medium.

17. A device according to claim 14, wherein it comprises an enclosure (E) through which at least two sheets of tubes (T) pass and in which the space between the tubes (T) is filled with capillaries (C) parallel to said tubes, between two end micron sieves ($M'_1$, $M'_2$).

18. A device according to claim 2, wherein said sheet of tubes (T) in connection with said fresh nutrient medium inlet and outlet means are constructed so as to provide said second flow velocity of about 10 $\mu$m/s.

* * * * *